(12) United States Patent
Rose

(10) Patent No.: US 6,413,220 B1
(45) Date of Patent: Jul. 2, 2002

(54) SURFACE ACOUSTIC WAVE PERIODONTAL PROBE AND METHOD OF DETECTING PERIODONTAL DISEASE

(76) Inventor: Emery S. Rose, 31-77 32$^{th}$ St., Astoria, Queens, NY (US) 11106

( * ) Notice: Subject to any disclaimer, the term of this patent is extended or adjusted under 35 U.S.C. 154(b) by 0 days.

(21) Appl. No.: 09/674,974

(22) PCT Filed: May 5, 1999

(86) PCT No.: PCT/US99/09781
§ 371 (c)(1),
(2), (4) Date: Nov. 8, 2000

(87) PCT Pub. No.: WO99/58080
PCT Pub. Date: Nov. 18, 1999

Related U.S. Application Data
(60) Provisional application No. 60/084,744, filed on May 8, 1998, and provisional application No. 60/093,931, filed on Jul. 23, 1998.

(51) Int. Cl.$^7$ ................................................ A61B 8/06
(52) U.S. Cl. .......................... 600/449; 600/589; 433/72
(58) Field of Search ................................ 600/437, 442, 600/443, 587, 589, 449, 483, 459; 433/29, 23, 72, 75, 215, 216; 73/597, 625, 626; 33/513, 514

(56) References Cited

U.S. PATENT DOCUMENTS

| | | | | |
|---|---|---|---|---|
| 5,022,856 A | * | 6/1991 | Zimble | 433/29 |
| 5,115,813 A | * | 5/1992 | Ylander et al. | 600/437 |
| 5,239,997 A | * | 8/1993 | Guarino et al. | 600/587 |
| 5,255,685 A | * | 10/1993 | Parra | 600/483 |
| 5,518,008 A | * | 5/1996 | Cucchiaro et al. | 600/590 |
| 5,874,677 A | * | 2/1999 | Bab et al. | 433/215 |
| 6,030,221 A | * | 2/2000 | Jones et al. | 433/215 |
| 6,162,177 A | * | 12/2000 | Bab et al. | 600/459 |
| 6,190,318 B1 | * | 2/2001 | Bab et al. | 600/437 |

* cited by examiner

*Primary Examiner*—Marvin M. Lateef
*Assistant Examiner*—Ali M. Imam
(74) *Attorney, Agent, or Firm*—Dilworth & Barrese, LLP (57) ABSTRACT

An ultrasonic probe (10) for measuring the depth of detachment between a tooth (30) and the tooth's supporting tissue includes a probe head (12) having an ultrasonic transducer (35). An incident acoustic wave pulse (50) is transmitted through a coupling medium at a critical angle of incidence for refraction at the interface between the coupling medium and the tooth surface (29, 31) to effect modal conversion to a surface acoustic wave pulse along the surface of the tooth (30). The critical angle of incidence is established by means of an angular setting of the ultrasonic transducer (35) in the probe head (12), a combination of the aforementioned angular setting with the ability to rock the probe head (12) to find the critical angle of incidence, and/or a phased array implementation. The disclosure also includes an algorithm for determining the depth of detachment based on the time lapse between transmission and detection of the reflection of the acoustic wave pulses.

19 Claims, 7 Drawing Sheets

SURFACE ACOUSTIC WAVE PERIODONTAL PROBE AND METHOD OF DETECTING PERIODONTAL DISEASE

This application claims the benefit of provisional application Serial No. 60/084,744 filed on May 8, 1998 and provisional application Serial No. 60/093,931 filed on Jul. 23, 1998 both entitled "SURFACE ACOUSTIC WAVE PERIODONTAL PROBE".

BACKGROUND OF THE DISCLOSURE

1. Technical Field

This disclosure relates to diagnostic probes and methods of incorporating diagnostic probes for detecting periodontal disease. More particularly, the present disclosure relates to a non-invasive diagnostic probe which emits and analyzes surface acoustic waves to detect and diagnose periodontal disease.

2. Description of Related Art

The instrument and method disclosed herein is directed to the non-invasive detection and measurement of periodontal disease by means of measuring the depth of detachment of a tooth from its supporting tissue or cementum. Since the crown of a tooth comprises enamel and the root of a tooth comprises dentin, the acoustic impedances of these various tooth elements differ.

From the cementoenamel junction (a well defined boundary between the crown and the root) down towards the root, the tooth, under healthy conditions, is attached to supporting tissue by cementum. In the presence of periodontal disease, a portion of the root is detached from the supporting tissue thus forming a gap from the crown and root boundary downwardly into the gum. The depth and width of the gap differs depending on the extent of disease progression.

U.S. Pat. No. 5,100,318, entitled "ULTRASONIC METHOD AND APPARATUS FOR MEASURING THE PERIODONTAL POCKET" discloses a dental instrument which impinges an acoustic wave onto the gum surface adjacent to the tooth to be interrogated which creates a longitudinal compression wave well known in ultrasound imaging. However, it is not possible to measure a periodontal gap, i.e., periodontal disease, unless the gap between the tooth and the detached adjacent supporting tissue are on the order of more than about 1 wavelength of the aforementioned longitudinal compression wave which, unfortunately, does not allow for early detection of a disease condition. Moreover, the disease must progress to form an appreciable gap before the instrument detects a diseased condition.

For example, in the case of a gap of smaller dimension (1 wavelength of the compression wave), e.g., a simple detachment of the tooth from its support tissue with no appreciable gap or pocket, the aforementioned longitudinal compressional wave would be reflected from the gum to bone surface without wave propagation down the gap to detect a separation of the tooth from the surrounding support tissue. Moreover, the '318 device has no means of stabilizing the angle of the transmitted ultrasonic wave relative to the boundary between the tooth and the surrounding tissue due to the fact that the angle of incidence is rarely consistent and is typically defined by the random gum configuration of an individual patient which, in the case of the '318 patent, would cause unwanted reflections and inaccurate readings.

Problems with the '318 patent are further exacerbated by the near impossibility of perfectly aligning the axis of transmission of the ultrasonic probe head with the axis of the periodontal pocket without prior knowledge of the orientation of the periodontal pocket, i.e., the ledge of the gum is structured such that in most cases positioning the probe for an incident longitudinal wave which is collinear with a periodontal pocket is extremely difficult. If such alignment is not perfect, the reading will be very inaccurate due to reflections. Moreover, since it is known that the angle to produce a surface acoustic wave on the tooth, in the case of the probe head being rested on the gum, is a function of the longitudinal acoustic wave velocity of the gum and the surface acoustic wave velocity of the tooth, the probability that the gum ledge defines exactly the aforementioned angle of incidence with the probe head, in a given patient, is essentially zero. Thus, the use of the '318 instrument to produce a surface acoustic wave on the surface of the tooth is very difficult due to the sensitivity of the modal conversion to the angle of incidence of the probe head.

U.S. Pat. No. 5,755,571, entitled "DIFFERENTIAL MEASUREMENT PERIODONTAL STRUCTURES MAPPING SYSTEM" discloses an instrument which produces a longitudinal acoustic wave pulse which is transmitted down a water filled periodontal pocket wherein the depth is measured by means of the pulse and echo time of flight. This method still requires that the periodontal pocket have a gap between the tooth surface and the detached adjacent supporting structures on the order of the wavelength of the transmitted wave. If the gap is smaller (or if there is simply a detachment of the tooth from the tissue), this instrument is not capable of detecting the periodontal disease condition. Further, the '571 instrument is overly invasive in that a second probe is mechanically inserted beneath the tissue to establish the position of the cementoenamel junction. This is typically ineffective in the case where the gap between the tooth and adjacent supporting structure is smaller than the width of the second probe. The use of the '571 mechanical probe is further deleterious for post treatment use since it may impair the healing process by causing injury and detachment of healing tissue.

Thus, there exists a need to develop an instrument and method of detecting the early stages of periodontal disease, e.g., when only slight separation, i.e., a non-appreciable gap, has formed between the tooth surface and the supporting tissue.

SUMMARY

The instrument and method disclosed herein includes the generation of a surface acoustic wave pulse (hereinafter referred to as a "SAW pulse") on a crown surface of a tooth which propagates towards the root of the tooth. In the case of a healthy tooth anatomy, the generated SAW pulse will reflect from the cementoenamel junction and crown and root interface with essentially one strong reflection. This is due to the absence of a surface on which the wave can propagate.

In the presence of periodontal disease, the SAW pulse will strike the crown and root interface resulting in a transmission component and a reflection component in proportion with the acoustic impedance mismatch between the enamel and the dentin and the angle of incidence at the interface. The time of flight of the reflection portion is sensed and used as a datum for the measurement of the depth of detachment. The transmission portion continues travelling along the root surface of the tooth until it strikes a point where the tooth is attached to the support tissue where it is then reflected due to the abrupt change in acoustic impedance at the attachment point. This second reflection constitutes a time of flight which is proportional to the depth of tooth detachment of the root since the SAW pulse has a fixed velocity depending on the medium in which it propagates. It is envisioned that due to boundary conditions, the SAW pulse will follow the irregular contour of the tooth as it propagates.

Modal conversion from a longitudinal acoustic wave pulse in the matching layer and compliant coupling medium to a SAW pulse propagating along the surface of the tooth toward the root takes place after refraction across the boundary between the compliant coupling medium and the tooth surface. The critical angle of incidence to convert the longitudinal acoustic wave pulse to a SAW pulse is a function of the longitudinal acoustic wave velocity of the coupling medium in contact with the tooth surface and the SAW pulse velocity on the tooth surface. The calculation of this angle is well known and defined in the literature: [sin(critical angle)=Vi/Vs]—where Vi is the acoustic wave velocity of the incident longitudinal wave in the coupling medium and Vs is the SAW velocity on a tooth surface.

It is also well known that the SAW pulse velocity is a function of material parameters such as the elastic constant and density of particular materials and is described in the literature, e.g., Ristic, *Principles of Acoustic Devices,* John Wiley and Sons, Inc., 1983, p.95. The SAW velocity is lower in a medium than the longitudinal acoustic wave velocity thus providing the additional benefit of better resolution due to a shorter wavelength at any given frequency, and allowing a lower frequency of operation for the minimum required resolution.

An electronic microcontroller controls the transmission of acoustic pulses by means of a gated oscillator or a pulse generator connected to an amplifier and matching circuit to drive a piezo or other acoustic wave transmitting transducer. When the transmission of the initial acoustic wave pulse is complete, the microcontroller gates the transducer to a receiver which samples the transducer at fixed time increments while storing the samples in progressive memory locations. The microcontroller then computes the depth of tooth detachment from the supporting tissue based on the elapsed time between the detection of the reflected SAW pulses. The elapsed time is directly calculable from the memory location or locations in which the reflection is stored in that each memory location is coincident with a particular elapsed time after the initial acoustic wave pulse transmission.

It is one object of the present disclosure to provide a non-invasive apparatus and method for detecting and accurately measuring periodontal disease at its earliest stages manifested by detachment of the tooth from adjacent supporting tissue without an appreciable gap or space therebetween heretofore not possible with the prior art.

A further object of the invention is to provide a periodontal probe capable of generating a SAW pulse and detecting its reflection on the tooth surface in a direction of propagation collinear with the root and supporting tissue to reproduceably and accurately measure a periodontal disease condition absent the presence of an appreciable gap or pocket between the tooth and its supporting tissue.

A further object of the invention is to provide a probe capable of ultrasonically measuring periodontal detachment by angularly manipulating the probe head with the tooth surface such that a modal conversion from a longitudinal acoustic wave pulse to a SAW pulse takes place at the interface between the probe head and the tooth surface.

Another object of the present disclosure is to provide an ultrasonic probe which includes a monitor for displaying the depth of detachment of a tooth surface from the supporting tissue and a device for recording the depth measurements with correlation to a particular tooth.

DETAILED DESCRIPTION OF THE PREFERRED EMBODIMENTS

Turning now to the drawings in which like reference numerals identify similar or identical components throughout several views, there is illustrated an acoustic wave periodontal probe in accordance with the principles of the present disclosure generally identified by reference numeral 10. Probe 10 includes a probe head 12 which is preferably made from a rigid polymer material, e.g., polyetherimide or ULTEM™ manufactured by Westlake Plastics, and which is attached to a handle 14 by way of a pivot 13. In some cases, it may be preferable to removably attach contact pad 40, probe head 12, and/or handle 14 and cable 18 depending upon a particular purpose, e.g., sterilization. It is also envisioned that the probe 10 could be provided with a profilaxis which would be discarded after use thus avoiding the need for resterilization. This profilaxis could simply be a latex or other disease impermeable sleeve which fits over the probe 10.

Figure 1:
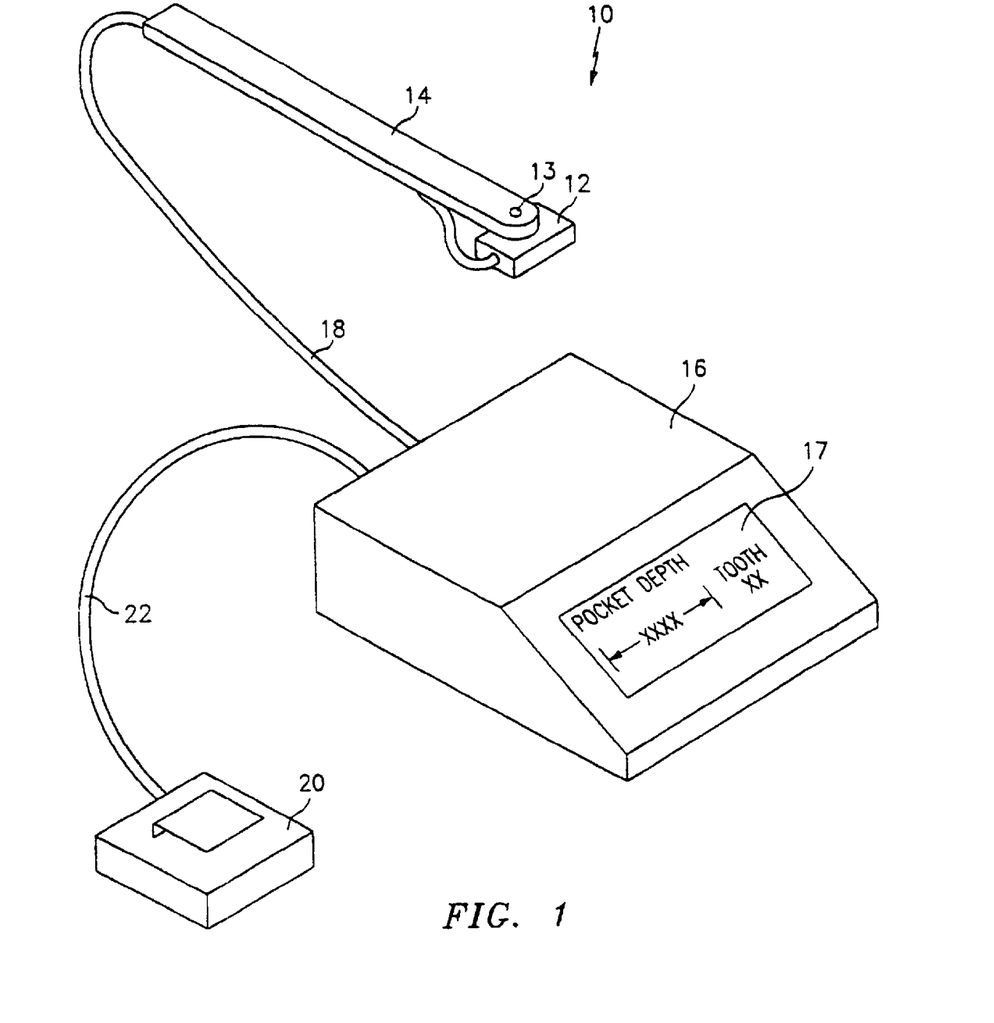
FIG. 1 is a perspective view of a periodontal probe according to the present disclosure.

Handle 14 is attached to a housing 16 by way of a cable 18 which electrically couples the probe head 12 and the internal acoustic components contained therein to the electrical components in housing 16. It is envisioned that probe head 12 generates and transmits a surface acoustic wave (SAW) pulse on the tooth surface which is subsequently analyzed by a microcontroller 121 (See FIG. 3) disposed within the housing 16 and displayed on a display screen 17 which will be described in more detail with respect to FIG. 3. A foot switch 20 is connected to the housing 16 by way of a cable 22 which enables an operator to selectively and remotely activate the probe head 12 to generate a SAW pulse along the tooth surface.

It is contemplated that the probe head 12 can be manipulated in the mouth of a dental patient by pivoting probe head 12 about handle 14 by means of a friction pivot 13. The probe head 12 may also be rotated in relation to elongated handle 14 and held in angular position by friction. The ability to rotate probe head 12 relative to elongated handle 14 is necessary for proper positioning of the instrument 10 in the mouth of the patient over the entire dental anatomy.

Figure 2:
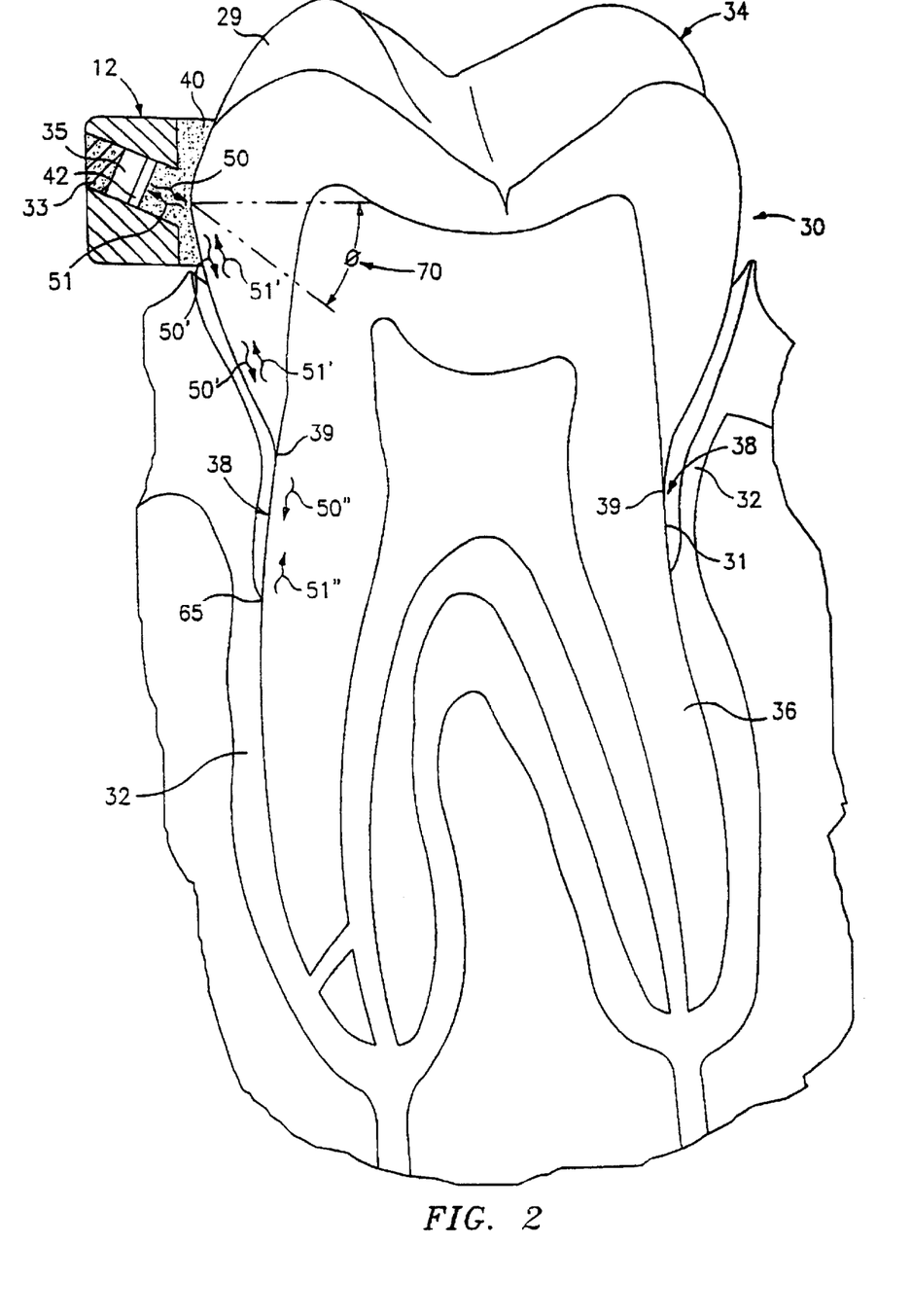
FIG. 2 is a cross-sectional view of a probe head of the periodontal probe housing an ultrasonic transducer shown transmitting an acoustic wave at the surface of a tooth through a compliant contact pad to generate a SAW pulse on the surface of the tooth.

Turning now to FIG. 2 which shows an enlarged view of a tooth 30 attached to the supporting tissue by cementum 32. Under healthy conditions, a root portion 36 of a tooth 30 is completely seated within cementum 32 with no distinguishable spaces formed between the tooth 30 and the supporting cementum 32. In contrast, the formation of a periodontal pocket or gap, e.g., 38, between the supporting tissue of the cementum 32 and the tooth 30 (or teeth) is an indication of periodontal disease such as periodontosis—the degeneration of connective tissue elements of the periodontal ligament. As mentioned above, the physical limitations of the prior art dental instruments of the past, e.g., inability to detect small periodontal pockets 38 between the supporting tissue of the cementum 32 wherein the gap between the root and adjacent structure is smaller than a longitudinal acoustic wavelength, make it very difficult to diagnose early formation of periodontal disease. Typically, only during the later stages of the development of the disease, i.e., after the formation of an appreciable pocket 38, do these devices register a diseased condition.

As shown in FIG. 2, a contact pad 40 is attached to the face of the probe head 12 and, during operation, is positioned against the crown surface 29 of the tooth 30 proximate the gum line. It is contemplated that the probe head 12 can be manipulated at various angles along the tooth 30 to establish the critical angle of incidence. Preferably, contact pad 40 is manufactured from a compliant material, e.g., RTV (silicon rubber) along with other well known filler materials, e.g., tungsten which provides acoustic coupling between a matching layer 42 disposed within the probe head 12 and the tooth 30 by conforming with the irregular contour of the crown surface 29. It is contemplated that the aforementioned compliant material of contact pad 40 may be blended so as to provide both an acoustic impedance which matches the crown surface 29 to minimize possible reflection and an acoustic velocity which is slower than that of the SAW pulse velocity on crown surface 29 so that SAW pulses can be generated through refraction at the interface at a critical angle of incidence 70 which will be explained in more detail below.

Preferably, the thickness of contact pad 40 between the area which abuts the crown surface 29 and the face of probe head 12 is dimensioned to allow the compliant material to compress and conform with the irregularities of crown surface 29 while also allowing the operator to arc, i.e., manipulate, the instrument 10 (about ten degrees of angular adjustment) such that the critical angle of incidence 70 for modal conversion can be attained by slight rocking of probe head 12. Preferably, contact pad 40 is removable and/or selectively attachable to the probe head 12, e.g., friction fit, and is designed for a single use. A backing material 33 is preferably attached to the transducer 35 to produce desirable acoustic wave pulse characteristics.

An ultrasonic transducer 35 is disposed within the probe head 12 and upon activation of the footswitch 20 transmits an ultrasonic wave pulse 50 at a frequency of anywhere between about 3 megahertz to about 25 megahertz giving up to about 0.1 mm resolution. As a result, a SAW pulse 50' is generated and propagates along the surface 29 of a crown 34 of tooth 30 until it strikes an interface point 39 between the crown 34 and root 36 where there is a reflection 51' and a transmission portion 50" of the original SAW wave pulse 50' which is proportional to the acoustic impedance difference between the two tooth surfaces 29 and 31. It is contemplated that the reflected SAW pulse 51' propagates in the opposite direction from the incident wave to strike the interface between contact pad 40 and crown surface 29 where a portion of it undergoes modal conversion to a reflected longitudinal wave 51 in contact pad 40 at the same angle 70 as the transmitted longitudinal acoustic wave pulse 50. Reflected longitudinal acoustic wave pulse 51 strikes ultrasonic transducer 35 causing an electrical impulse which enables measurement of the time of flight of the SAW pulse 50' and echo 51' from the crown and root interface 39.

After contacting the interface 39 between the crown 34 and the root 36, a portion 50" of the SAW wave 50' continues along the surface 31 of the root portion 36 of the tooth 30 until it strikes a point of tooth attachment 65 within the cementum 32 where an echo 51" of the SAW pulse 50" is reflected back towards the probe head 12. In the case of periodontal detachment, i.e., a distinguishable pocket 38 formed between the tooth 30 and the cementum 32, SAW pulse reflection 51" from tooth attachment point 65 will strike the interface between crown surface 29 and contact pad 40 where it will undergo modal conversion to a longitudinal acoustic wave pulse 51 in contact pad 40. Longitudinal acoustic wave pulse 51 will then strike ultrasonic transducer 35 and cause an electrical impulse enabling measurement of the time of flight of the SAW pulse 50' and reflected pulse 51" from attachment point, 65. The periodontal detachment depth is the distance between crown and root interface 39 and point of attachment 65 between root 36 and support tissue 32. This detachment distance can now be calculated as a function of the difference between the two aforementioned times of flight of the SAW pulse 50' and the reflected SAW pulses 51' and 51".

Figure 3:
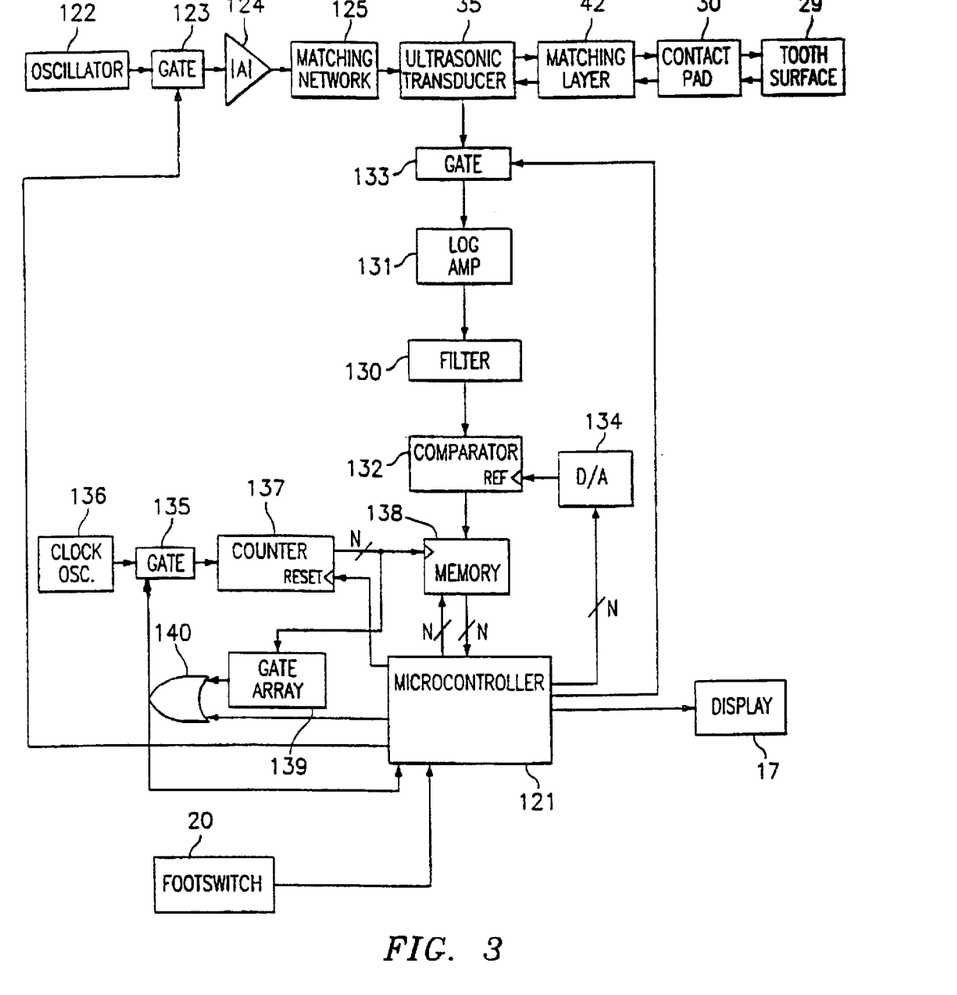
FIG. 3 is a diagrammatic representation of the circuitry of the present disclosure.

FIG. 3 shows the internal circuitry of the housing 16 in diagrammatic form. More particularly, the circuitry includes a microcontroller 121 programmed to periodically initiate an electronic pulse (typically between one and ten cycles) from an oscillator 122 through a gate 123 at either the resonant frequency of an ultrasonic transducer 35 or in a "chirp" (a sinusoidal signal that increases or decreases its frequency linearly with time for a fixed duration of time). Preferably, the electrical signal from oscillator 122 is amplified by a power amplifier 124 which propagates through a matching network 125 to the ultrasonic transducer 35 where it is then converted to an ultrasonic longitudinal acoustic wave pulse 50. It is contemplated that the ultrasonic longitudinal acoustic wave pulse 50 propagates through matching layer 42 and contact pad 40 and to form SAW pulse 50' on the crown surface 29 due to refraction at the critical angle of incidence 70.

Slightly after the generation of the transmitted signal, ultrasonic transducer 35 is electrically coupled through an electronic gate 133 to a logarithmic amplifier 131, a filter 130 and a first input to comparator 132. After reflection from a point of discontinuity in acoustic impedance along crown surface 29, the SAW pulse 50' will reverse its direction of propagation and pass through the interface between contact pad 40 and crown surface 29 where longitudinal wave 51 is generated and propagates in a direction toward ultrasonic transducer 35. Ultrasonic transducer 35, upon being struck by the reflected longitudinal wave 51, responds by generating an electrical signal in proportion to the amplitude of the striking longitudinal wave 51 which propagates through electronic gate 133, logarithmic amplifier 131 and filter 130 to the first input to comparator 132. A second input to comparator 132 from a digital-to-analog converter 134 is designed as a reference voltage level and is derived from microcontroller 121. It is contemplated that the comparator 132 will change its output state if the amplitude of the reflected ultrasonic acoustic wave 51 is higher than a level proportional to the reference voltage output by digital-to-analog converter 134.

After initial excitation of transducer 35 by the activation of electronic gate 123, microcontroller 121 activates an electronic gate 135 enabling a clock oscillator 136 to drive counter 137 which increments the address of memory 138 at the frequency of oscillation of the clock oscillator 136. A small delay is implemented between the pulsing of electronic gate 123 and activation of electronic gate 135 through OR gate 140 and electronic gate 133 to allow any transients (typical of initial excitation of ultrasonic transducer 35) to settle. If the output of comparator 132 changes state at any time during an echo reception period, a digital "1" will be recorded at the memory location proportional to the time of flight of the SAW pulse 50' on surface of tooth 30.

A gate array 139 compares the address asserted by counter 137 to a memory 138 with a reference value stored in a gate array 139 which is proportional to the maximum time allotted for a valid echo reception. When the address to memory 138 from counter 137 matches the aforementioned reference in gate array 139, gate 135 will be disabled by the output of gate array 139 through OR gate 140. Microcontroller 121 then interrogates external memory 138 by checking each address location for digital "1s". Microcontroller 121 then asserts a disable to gate 135 through OR gate 140 and resets counter 137 which allows another pulse and echo cycle to be initiated.

It is envisioned that the discrete logic components are incorporated into a single programmable gate array stored in the instrument housing 16, however, certain of the above logical components can also be disposed within other elements of the instrument 10, e.g., probe head 12 or handle 14. Preferably, the circuitry of the gate array is initiated by activation of footswitch 20 and the output of the array is displayed on the electronic display 17 (See FIG. 1).

Figure 4:
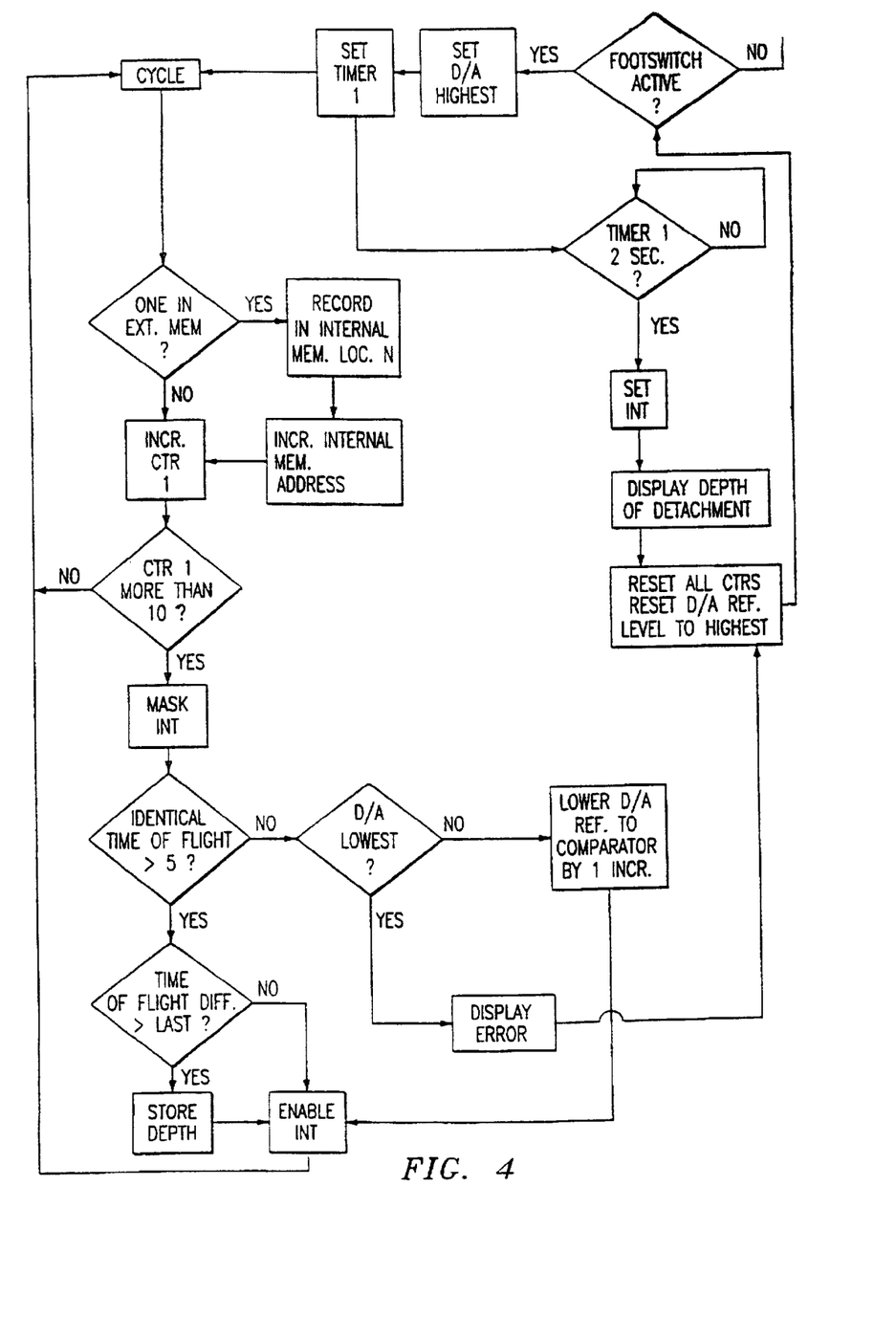
FIG. 4 is a logic chart of the algorithm used to detect a periodontal condition.

As best illustrated by the FIG. 4 flow diagram, upon depression of footswitch 20, microcontroller 121 initiates the algorithm starting with the highest setting of the analog reference voltage to comparator 132 through digital-to-analog converter 134 and initialization and activation of an internal timer for an interrupt to occur after two seconds. Preferably, ten cycles are performed. Each cycle is comprised of an initial acoustic wave pulse 50 and an aforementioned period of time for echo reception after which microcontroller 121 interrogates external memory 138 for the presence of digital "1s". Preferably, each external memory location coincides with a specific time of flight. A first digital "1" represents the echo 51' from root and crown interface 39 and a second represents the echo 51" from tooth surface attachment point 65. If root and crown interface 39 and point of tooth attachment 65 are coincident, as they would be in a healthy dental anatomy, there will be only one strong echo.

In each cycle, microcontroller 121 records the addresses of the external memory locations in which digital "1s" are found in a first block of twenty internal memory locations. Each two consecutive memory locations represent the two aforementioned echoes of interest in one of the ten cycles. After completion of the ten cycles, microcontroller 121 analyzes the twenty locations in the aforementioned first block of its internal memory. If five or more identical time of flight pairs are found, microcontroller 121 assumes this value to be processed as valid time of flight. If only one echo (within a predetermined maximum time of flight to a normal cementoenamel junction) is found with five or more identical times of flight, microcontroller 121 assumes this value to be processed as a valid time of flight indicating no depth of detachment. The interrupt is masked while the aforementioned calculation is being made.

Microcontroller 121 maintains a second single internal memory location separate from the aforementioned twenty locations where it stores the longest calculated time of flight difference between the echo 51' from crown and root interface 39 and echo 51" from point of tooth attachment 65. Microcontroller 121 compares the newest valid time of flight difference with any prior recording of a valid time of flight difference in the aforementioned second of its internal memory locations and stores the new value in this single memory location only if it is the longer of the two. If five or more identical times of flight are not found in ten of the aforementioned cycles, microcontroller 121 decrements the analog reference voltage level to the input of comparator 132 by means of digital-to-analog converter 134 unless a preset lowest limit has been reached. If the preset lowest limit has been reached, microcontroller 121 displays an error on display 17 and resets the counters and resets digital-to-analog converter 134 to the highest setting and returns to polling footswitch 20. The operator must then reposition probe head 12 on crown surface 29 so as to achieve a better acoustic coupling and then depress footswitch 20.

If the preset lowest limit has not been reached, the algorithm proceeds and microcontroller 121 enables a timer interrupt and continues the aforementioned cycling until an internal timer interrupt occurs. An internal timer interrupt after about two (2) seconds of measurement causes microcontroller 121 to stop the aforementioned algorithm, calculate the depth of the periodontal detachment 65 as a function of the longest valid time of flight difference, reset all counters and reset digital-to-analog converter 134 to the highest level. Microcontroller 121 then returns to polling footswitch 20 for another measurement.

Figure 5:
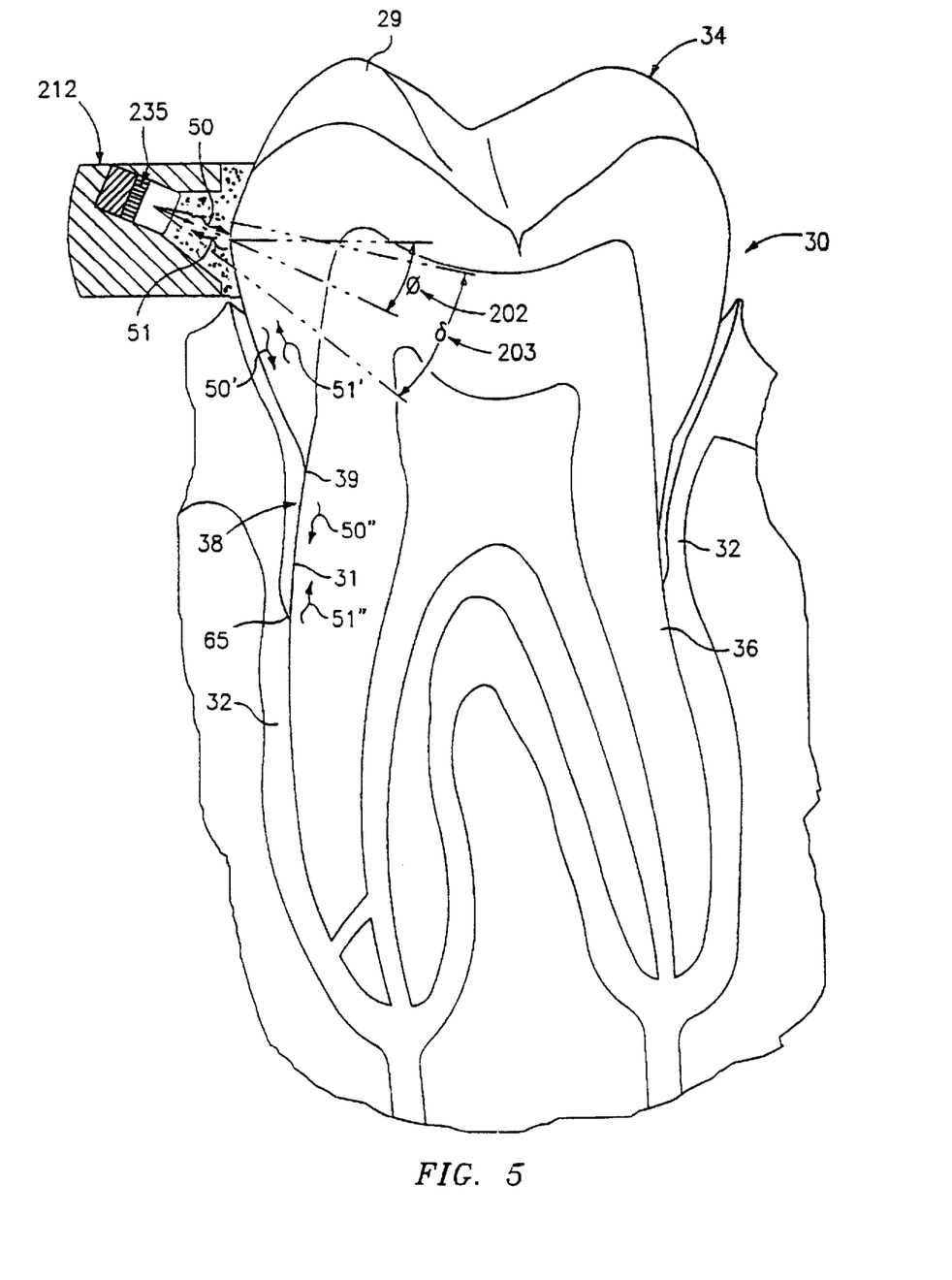
FIG. 5 shows another embodiment of the present disclosure incorporating a phased array transducer used for beam steering and discerning an angle of incidence of a received acoustic wave.

FIG. 5 shows another embodiment of the present disclosure wherein a segmented transducer 235 is used as a phased array for beam steering the transmitted acoustic wave pulses 50. As already stated, irregular curvatures on the crown surface 29 of the tooth 30 are such that the position of probe head 212 with crown surface 29 may not always be perfectly aligned at the critical angle of incidence 202 for the aforementioned modal conversion of the incident longitudinal acoustic wave pulse 50. Using a segmented transducer 235 as a phased array for beam steering precludes the necessity for the operator to slowly rock probe head 12 while using the instrument. Microcontroller 221 steers the longitudinal acoustic wave 50 through a fraction of correction angle 203 centered about critical angle of incidence 202 at the end of each ten SAW pulse and echo cycles.

Figure 6:
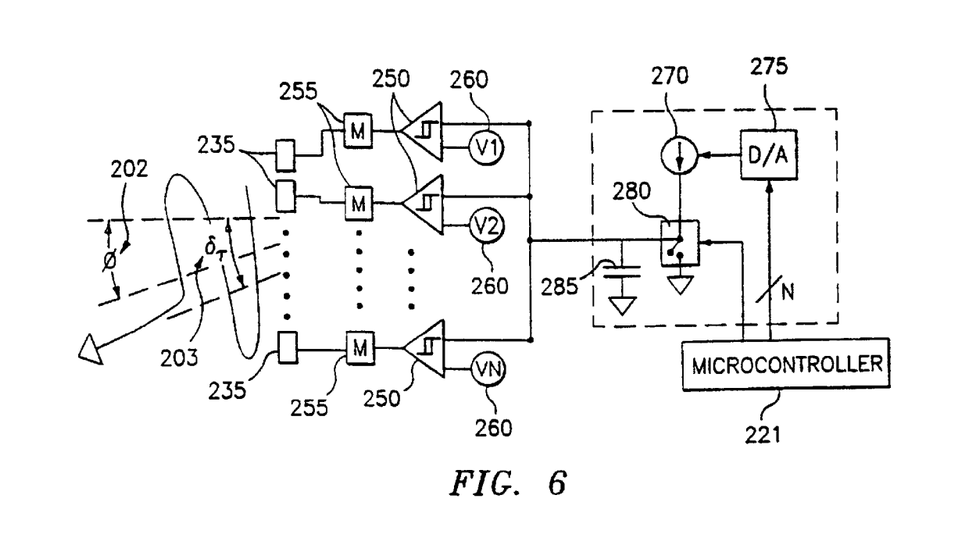
FIG. 6 is a diagrammatic representation of the phased array transducer and driving circuitry.
Figure 7A:
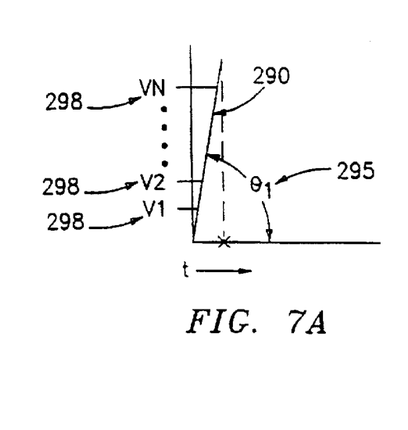
FIGS. 7A and 7B are graphical illustrations of the signals which control and drive the phased array transducer.

As illustrated by FIGS. 5 and 6, phased array transducers 235 are preferably driven by switching amplifiers 250 and matching networks 255. More particularly, a first input terminal of switching amplifiers 250 is connected to reference voltage sources 260. When the voltage on the second input to switching amplifiers 250 exceeds the reference voltage input by reference voltage sources 260, array transducers 235 will be driven by electrical pulses from the outputs of switching amplifiers 250 through matching networks 255. The voltages imparted by reference voltage sources 260 to switching amplifiers 250 are a range from a minimum to a maximum in equal increments as best illustrated by FIG. 7. The correction angle 203 of the transmitted acoustic wave is controlled by microcontroller 221 by means of its setting of current flow in an adjustable current source 270 through a digital-to-analog converter 275. Microcontroller 221 opens a switch 280 when it comes to a point in its algorithm wherein array 235 is to be actuated. When switch 280 is opened, current from current source 270 will charge a capacitor 285 connected to the second input of each of switching amplifiers 250.

Figure 7B:
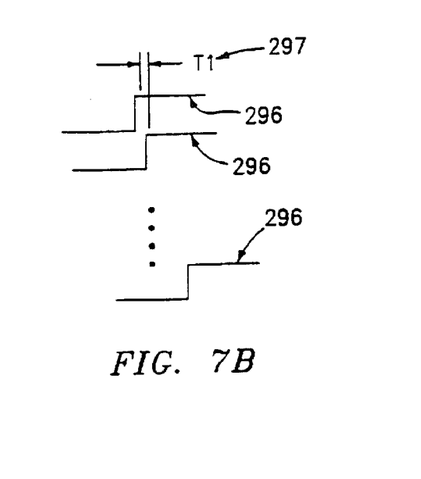

It is contemplated that the voltage output from capacitor 285 will be a linear ramp 290 over time with the angle 295 being determined by the setting of the current source 270. Amplifiers 250 will each output an electrical pulse 296 when the voltage being impressed by voltage ramp 290 on the second of the inputs to switching amplifiers 250 exceeds each of the reference voltages 298. The time delay 297 between the output pulses 296 of each of the switching amplifiers 250 and, thus, the time delay between excitation of array elements 235, is a function of angle 295. It is known that the transmitting angle 203 of the acoustic wave pulse 50 is a function of the delay time 297 between excitation of array transducers 235.

Figure 8:
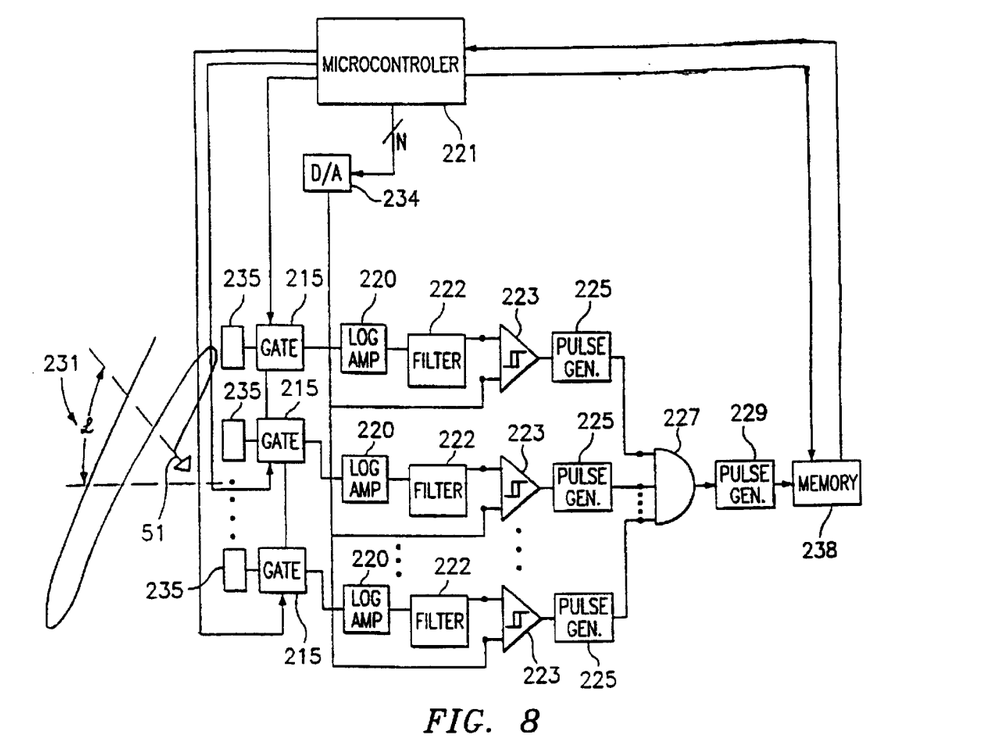
FIG. 8 is a diagrammatic representation of the phased array and receiving circuitry.
Figure 9:
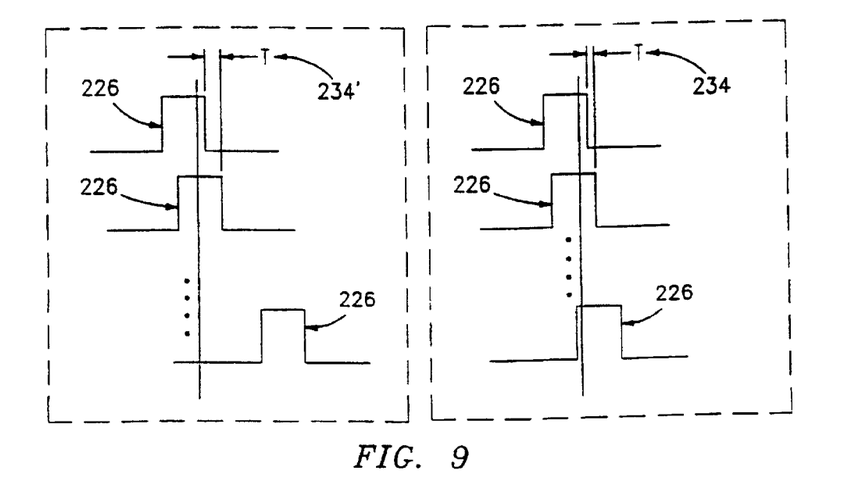
FIG. 9 is a graphical illustration of the signals used for discerning the angle of incidence of the received acoustic wave.

FIGS. 8 and 9 show a method of discerning an angle of incidence 231 of a received wave and filtering the registration of the received wave in external memory 238 as a function of angle of incidence 231. Incoming reflected wave 51 strikes array transducers 235 at angle of incidence 231 causing a time delay 234 (See FIG. 9) between excitation of each of array transducers 235. Gates 215 controlled by microcontroller 221 disable signal transmission to logarithmic amplifier 220 and successive signal conditioning members while array traducers 235 are being driven to output an initial acoustic wave pulse transmission. Microcontroller 221 enables signal reception by array transducer elements 235 through gates 215 to propagate through logarithmic amplifiers 220 and filters 222 to a first input to comparators 223.

When the amplitude of the electrical signal of each of array transducers 235 exceeds a level proportional to the reference voltage level imparted to the second input of electronic comparators 223 by digital-to-analog converter 234, the outputs of each of electronic comparators 223, respectively, will transition to a high state. When the output of any one of electronic comparators 223 transitions to a high state, a succeeding edge triggered pulse generator 225 outputs a pulse 226 of predetermined duration. The outputs of each of the pulse generators 225 are connected to the input of an AND gate 227.

If the delay time 234 between electronic pulses 226 from the outputs of pulse generators 225 to the input of AND gate 227 is small enough such that there is a point in time wherein pulses 226 are all in the high state at the same time, the output of AND gate 227 will transition to a high state. When the output of AND gate 227 transitions to the high state, edge triggered pulse generator 229 outputs a pulse of predetermined duration to the input of external memory 238 so as to register a valid reception of a reflected acoustic pulse. If the angle of incidence 231 is outside of a tolerance within which it could be assumed that acoustic wave pulse 51 is a valid reflection from tooth surface 34 no registration will be entered in external memory 138. A time delay 234' which results in pulses 226 never being aligned at any one point in time is a result of a spurius, invalid reflection due to imperfect acoustic matching, or sidelobes. As a result, the output of AND gate 227 will never change state and the output of pulse generator 229 will never change state and there will be no registration of the event in external memory 238. The tolerance within which the angle of incidence 231 is considered valid is a function of the width of pulses 226 generated by pulse generators 225. Microcontroller 221 adjusts the voltage reference level to the first input of comparators 223 so that an algorithm such as the one described in FIG. 4 can be executed.

In use, the electronic microcontroller 121, 221 initiates a series of acoustic wave pulse and echo cycles in rapid succession while the operator slowly rocks the probe head 12 (or the acoustic wave pulse beam is steered through a predetermined angle in the case of a phased array transmitter) with the compliant contact pad 40 in contact with the target tooth 30. The acoustic wave pulse and echo cycle time, including the time of flight plus the time for information processing, is approximately one hundred microseconds, which makes it possible to generate 10 of the aforementioned cycles per millisecond. At this rate of cycling, the rocking motion of the user (or beam steering) is a quasi-static process over which the microcontroller 221 tests all angles within an arc. This is necessary due to the irregular contour of the crown surface 29 of most teeth.

At one point in the rocking sequence (or beam steering), the critical angle of incidence 70, 202 will have been established with the largest virtually plane area of the crown surface 29. If the microcontroller 221 detects two sufficiently large reflections over the longest time of flight at a particular point in the aforementioned process, it records this as a periodontal pocket with a depth measurement. In the case of one large reflection, a healthy tooth anatomy is indicated.

It is envisioned that the compliant contact pad 40 bears against the matching layer 42 in the probe head at one end and conforms at the other end with the irregular crown surface 29 to establish intimate contact for acoustic coupling. The critical angle of incidence to generate a SAW pulse on the surface 29 of the tooth is essentially established by the angular relationship between the setting of the ultrasonic transducer and matching layer 42 in the probe head 12 and the face of the probe head 12.

It is further envisioned that the computational algorithm for discerning the critical angle of incidence includes a fuzzy logic algorithm. Moreover, it is contemplated that the present disclosure can also be used to measure an advanced periodontal condition, i.e., a larger periodontal pocket.

From the foregoing and with reference to the various figure drawings, those skilled in the art will appreciate that certain modifications can also be made to the present disclosure without departing from the scope of thereof. For example, it is envisioned that detection of the reflected SAW pulse can be accomplished by using the same transducer as both a detector and a transmitter. It is also envisioned that transmission and detection of the aforementioned acoustic waves can be accomplished by two or more separate transmitting and receiving transducers or transducer arrays. Preferably, the operational frequency of the instrument of the present disclosure is between 3 and 25 megahertz. Higher frequencies of operation allow better lateral resolution because the area of the transducer can be smaller with a longer near field, and a smaller angle of beam divergence in the far field. The higher frequencies will, however, attenuate faster.

It is also contemplated that at the aforementioned rate of cycling wherein the rocking motion of the user in combination with the microcontroller and execution of the fuzzy logic algorithm which tests all angles within an arc, the compliant coupling medium can include a ledge of a patient's gum.

While the aforementioned method of signal processing is fast and economical, it is certainly not the only method. A more conventional method of signal processing would be to fill a memory with samples from an analog-to-digital converter at a rate above Shannon's lower limit, i.e., the minimum sampling rate of a digital system processing analog signal. The sampling rate must be at least twice the maximum frequency of the highest frequency of signal being processed (or sampled), after which a DSP (digital signal processing) chip such as the TMS320C30 chip manufactured by Texas Instrument would do signal processing to retrieve the relevant echoes. A convolution or correlation operation would provide the ability to discern the relevant signals. If the ultrasonic transducer were driven with a chirp, a maximum signal to noise power ratio would be achieved as well as optimal resolution.

There have been described and illustrated herein several embodiments of a non-invasive diagnostic probe which emits and analyzes surface acoustic waves to detect and diagnose periodontal disease. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplications of preferred embodiments. Those skilled in the art will envision other modifications within the scope and spirit of the claims appended hereto.

What is claimed is:

1. An ultrasonic probe for measuring the depth of detachment between a tooth and the tooth's supporting tissue, comprising:
   a probe head having ultrasonic transducer means for transmitting acoustic wave and detecting acoustic wave pulses and a coupling medium for communicating acoustic wave pulses between said ultrasonic transducer and the tooth surface;
   means for angularly aligning the transmission of acoustic wave pulses emanating from said ultrasonic transducer through said coupling medium to obtain an angle of incidence between the tooth surface and said acoustic wave pulse in said coupling medium to effect a modal conversion from an incident acoustic wave pulse in said coupling medium to a surface acoustic wave pulse along the tooth surface upon refraction of the said incident acoustic wave pulse across a boundary between said coupling medium in contact with the tooth surface; and
   means for measuring the depth of the tooth detachment as a function of said modal conversion from an incident acoustic wave pulse in said coupling medium to said surface acoustic wave pulse along the tooth surface upon refraction of said incident acoustic wave pulse across said boundary between said coupling medium and the tooth surface.

2. An ultrasonic probe according to claim 1 wherein said measuring means comprises:
   means for tracking a time lapse from the transmission of said acoustic wave pulses to the detection of the reflection of said acoustic wave pulses; and
   means for comparing a reference datum to said time lapse to determine the depth of detachment between the tooth surface and the tooth's supporting tissue.

3. An ultrasonic probe according to claim 2 wherein said reference datum is the crown and root interface of a tooth.

4. An ultrasonic probe according to claim 1 further comprising means for displaying the depth of detachment of the tooth surface from the supporting tissue.

5. An ultrasonic probe according to claim 1 wherein said transducer is activated remotely.

6. An ultrasonic probe according to claim 1 wherein said ultrasonic transducer is segmented to form a phased array to enable detection of the received angle of incidence of the acoustic wave pulse.

7. An ultrasonic probe according to claim 1 wherein said ultrasonic transducer is segmented to form a phased array to enable control of said transmitted angle of incidence of said acoustic wave pulse such that said transmitted angle of incidence is optimized for the modal conversion of said incident acoustic wave pulse to said surface acoustic wave pulse along the tooth surface.

8. An ultrasonic probe according to claim 7 wherein said ultrasonic transducer also enables detection of a received angle of incidence of the acoustic wave pulse.

9. An ultrasonic probe according to claim 1 further comprising a compliant contact member disposed between said probe head and the tooth surface which enables said probe head to rock so as to establish an optimal angle of incidence between said probe head and the tooth surface for modal conversion between an acoustic wave pulse and a surface acoustic wave pulse upon refraction between said compliant contact member and the tooth surface.

10. An ultrasonic probe according to claim 9 further comprising computing means for repeated testing of acoustic wave pulse and echo signals and discerning a point in said rocking of said probe head wherein a critical angle of incidence is established.

11. An ultrasonic probe according to claim 10 wherein said computing means for repeated testing of acoustic wave pulse and echo signals and discerning a point in said rocking of said probe head wherein a critical angle of incidence is established is operative automatically and with a speed of cycling, relative to human motion, that enables all angles of incidence within said rocking motion to be tested.

12. An ultrasonic probe according to claim 11 wherein the computational algorithm for discerning the critical angle of incidence is a fuzzy logic algorithm.

13. An ultrasonic probe according to claim 1 further comprising means for displaying the depth of detachment of a tooth surface from the supporting tissue and means for recording the depth of detachment of a tooth surface with correlation to a particular tooth.

14. An ultrasonic probe for measuring the depth of detachment between a tooth and the tooth's supporting tissue, comprising:
   a probe head having a phased array ultrasonic transducer means for transmitting and steering acoustic wave pulses and detecting an angle of incidence of received ultrasonic acoustic wave pulses and a coupling medium for communicating said acoustic wave pulses between said ultrasonic transducer and the tooth surface;
   said probe head maintaining said phased array ultrasonic transducer means and said coupling medium in communication with the tooth surface through said coupling medium to effect modal conversion from an incident acoustic wave pulse at a critical angle of incidence in said coupling medium to a surface acoustic wave pulse across a boundary between said coupling medium in contact with said tooth surface;
   means for tracking a time lapse from the transmission of said acoustic wave pulses to the detection of the reflections of said acoustic wave pulses; and
   means for comparing a reference datum to said time lapse for determining the depth of detachment between the tooth surface and the tooth's supporting tissue with reference to a datum.

15. An ultrasonic probe according to claim 14 wherein said reference datum is the crown and root interface of a tooth.

16. An ultrasonic probe according to claim 14 further comprising computing means for repeated testing of acoustic wave pulse and echo signals and discerning a point in said beam steering of said phased array transducer means wherein an angle of incidence for modal conversion to a surface acoustic wave pulse is established.

17. An ultrasonic probe according to claim 16 wherein said computing means for repeated testing of acoustic wave pulse and echo signals and discerning a point in said beam steering of said phased array transducer wherein said angle of incidence is established is operative automatically and with a speed of cycling, relative to human motion, that enables all angles of incidence within said beam steering to be tested.

18. An ultrasonic probe according to claim 17 wherein the computational algorithm for discerning said angle of incidence is a fuzzy logic algorithm.

19. A method for measuring the depth of detachment between a tooth and the tooth's supporting tissue, comprising the steps of:

provided a probe head having an ultrasonic transducer for transmitting acoustic wave pulses and detecting acoustic wave pulses and a coupling medium for communicating said acoustic wave pulses between said ultrasonic transducer and the tooth surface;

angularly aligning said ultrasonic transducer to produce an acoustic wave pulse in said coupling medium to obtain an angle of incidence between the tooth surface and said acoustic wave pulse in said coupling medium to effect a modal conversion from an incident acoustic wave pulse in said coupling medium to a surface acoustic wave pulse along the tooth surface upon refraction of the said incident acoustic wave pulse across a boundary between said coupling medium and the tooth surface; and measuring the depth of the tooth detachment as a function of said modal conversion from said incident acoustic wave pulse in said coupling medium to said surface acoustic wave pulse along the tooth surface upon refraction of said incident acoustic wave pulse across said boundary between said coupling medium and the tooth surface.

\* \* \* \* \*